United States Patent [19]

Maeda et al.

[11] Patent Number: 5,093,315
[45] Date of Patent: Mar. 3, 1992

[54] DIETING AGENTS COMPRISING ALPHA-AMYLASE INHIBITING SUBSTANCES FROM WHEAT

[75] Inventors: Koji Maeda, Heidelberg, Australia; Yoshikuni Suzuki, Ohmiya; Hidehiko Takahashi, Tokyo, all of Japan

[73] Assignee: Nisshin Flour Milling Co., Ltd., Tokyo, Japan

[21] Appl. No.: 692,780

[22] Filed: Apr. 26, 1991

Related U.S. Application Data

[63] Continuation of Ser. No. 447,232, Dec. 6, 1989, abandoned.

[30] Foreign Application Priority Data

Dec. 9, 1988 [JP] Japan .................. 63-311245

[51] Int. Cl.⁵ .............................................. A61K 37/00
[52] U.S. Cl. .......................................... 514/2; 514/951; 514/960
[58] Field of Search ............................ 514/2, 951, 960

[56] References Cited

U.S. PATENT DOCUMENTS

| | | | |
|---|---|---|---|
| 4,337,309 | 6/1982 | McGeeney | 435/22 |
| 4,806,626 | 2/1989 | Maeda et al. | 530/375 |
| 4,910,297 | 3/1990 | Zawistowska | 530/375 |

FOREIGN PATENT DOCUMENTS

| | | |
|---|---|---|
| 2081468 | 3/1971 | France . |
| 272274 | 10/1989 | German Democratic Rep. . |
| 57-012995 | 1/1982 | Japan . |
| 57-14072 | 8/1982 | Japan . |
| 60-004132 | 1/1985 | Japan . |
| 63-185995 | 8/1988 | Japan . |

OTHER PUBLICATIONS

Braithwaite et al., "Chromatographic Methods".
Belter et al.l, "Bioseparations, Downstream Processing for Biotechnology".
Chemical Abstracts, vol. 89, p. 211919g (1978).
Chemical Abstracts, vol. 108, p. 163908q (1987).
Chem. Abstracts 99, 84271U (1983), R. J. Westlake, et al.

Primary Examiner—Frederick E. Waddell
Assistant Examiner—K. Weddington
Attorney, Agent, or Firm—Michael N. Meller

[57] ABSTRACT

A dieting agent is disclosed which comprises an aqueous solution or a solid substance of a concentration α-amylase inhibiting substance which is produced by a process which comprises heat treating a supernatant fraction of an aqueous extract of wheat or wheat flour to modify unnecessary protein contaminants in the supernatant fraction, removing a modified protein from said fraction, subjecting a resulting aqueous solution containing an α-amylase inhibiting substance to a concentration treatment using an ultrafiltration membrane to form an aqueous solution of a concentrated α-amylase inhibiting substance or drying the aqueous solution. The dieting agent exhibits a body weight gain-inhibiting effect.

12 Claims, No Drawings

DIETING AGENTS COMPRISING ALPHA-AMYLASE INHIBITING SUBSTANCES FROM WHEAT

BACKGROUND OF THE INVENTION

1. Field of the Invention

This invention relates to a dieting agent comprising an α-amylase inhibiting substance produced from a supernatant of an aqueous extract of wheat or wheat flour.

2. Description of the Prior Art

It is known that wheat or wheat flour contains a large quantity of α-amylase inhibiting substances. Such substances inhibit conversion of starch to saccharides even if sprouting of wheat ears occurs under such weather conditions as much rain in harvest season thereby preventing quality deterioration of the harvested wheat.

On one hand, α-amylase is an enzyme capable of at random hydrolyzing the α-1,4-glycoside bond of starch, glycogen and the like, which is extensively distributed in animals, plants, molds, bacteria, etc. In humans, there are α-amylase of saliva origin and α-amylase of pancreas origin, which play a role in converting starch to saccharides respectively in the mouth and the digestive tracts. Because the α-amylase inhibiting substance inhibits an activity of α-amylase, it is useful as a dieting agent for the prevention of obesity, as therapeutic agents for hyperglycemia and diabetes, as prophylactic agent for dental caries and so on.

In these circumstances, many attempts have been made to produce an α-amylase inhibitor by extraction from various raw materials. There are known a method for the extraction from betel nuts (Japanese Patent LOP Publn. No. 185995/1988) and a method for extracting an α-amylase inhibiting substance contained in wheat (Japanese Patent LOP Publn. No. 140727/1982).

The prior art processes of preparing α-amylase inhibiting substances from wheat or wheat flour include a very complicated operation which comprises a heat treatment of an aqueous extract of wheat or wheat flour, fractional precipitation of the resulting mass with an organic solvent, collecting a precipitated fraction, treating a solution fraction with an adsorbent, eluting an adsorbed substance with a salt solution and fractionating an eluate by chromatography. These processes are not efficient and economical for the production of α-amylase inhibiting substances. Consequently, α-amylase inhibiting substances obtained by such prior processes will be expensive. In this circumstance, such an expensive α-amylase inhibiting substance as produced above has unavoidably been employed for a dieting agent which requires supply of α-amylase inhibiting substances in a large amount and at a low cost.

In the manufacture of wheat gluten and wheat starch, a large amount of washing (waste liquid) has been produced from a step of eluting starch from dough or batter formed by kneading flour and water. A treatment of waste liquid needs much labor and cost. This treatment includes a troublesome problem in the industry. Since such waste liquid contains α-amylase inhibiting substances, recovery of the substances from the waste liquid would bring about combined effects of disposing the waste liquid and collecting valuable substances. Therefore, efficient recovery of α-amylase inhibiting substances from the waste liquid and use of the recovered substance as a dieting agent would not only bring about a technical diversification but also produce a very remarkable technical and economical effect of simultaneously recovering valuable substances from waste liquid and disposing the waste liquid.

DETAILED DESCRIPTION OF THE INVENTION

The present invention is directed to a dieting agent comprising an aqueous solution or a solid substance of a concentrated α-amylase inhibiting substance which is produced by a process which comprises heat treating a supernatant fraction of an aqueous extract of wheat or wheat flour to modify unnecessary protein contaminants in the supernatant fraction, removing a modified protein from said fraction, subjecting a resulting aqueous solution containing an α-amylase inhibiting substance to a concentration treatment using an ultrafiltration membrane to form an aqueous solution of a concentrated α-amylase inhibiting substance or drying the aqueous solution.

An embodiment of the process steps for the preparation of the concentrated α-amylase inhibiting substances includes:

(a) Wheat flour and water at a ratio of at least 7:1 are kneaded at a temperature of 0 to 40° C. for a period of 30 min. to 3 hours followed by centrifugation (e.g., 3000 G, 30 min.) or allowing to stand to give a supernatant. The supernatant contains soluble substances such as soluble protein, soluble starch, inorganic salts and coloring matters.

(b) The supernatant is heated at a temperature of 70 to 95° C., preferably 85 to 90° C. to modify unnecessary proteins. The modified proteins are removed by centrifugation (e.g., 3000 G, 30 min.) or allowing to stand.

(c) The resulting supernatant is filtered as it is still hot preferably by filters having a pore size of 3 $\mu$m and 1 $\mu$m respectively to give a clear solution.

(d) Subsequently, the solution is passed through a microfiltration membrane having a pore size of 0.2 $\mu$m for sterilization.

(e) The sterilized solution containing α-amylase inhibiting substances is concentrated using an ultrafiltration membrane (preferably, a membrane passing through a fraction having a molecular weight of more than 20,000 to less than 100,000). Inorganic salts and unnecessary low molecular weight substances are removed but α-amylase inhibiting substances do not pass through said membrane. In this step, a volume of the clear solution is concentrated to less than about 1/10 of its original volume.

(f) Optionally, the concentrated solution is dried by a conventional method such as spray, freeze or vacuum drying to afford a powdery product.

The supernatant used in the step (a) may be a supernatant separated from a kneaded solution of wheat flour and water for the purpose of recovering α-amylase inhibiting substances or may be a waste liquid after recovery of gluten and starch from wheat.

In the manufacture of gluten and wheat starch, Martin's or Batter's method has been employed. A portion of the water used in such method is carried out of the manufacturing system as moisture to maintain the gluten in its wet state or as moisture contained in the starch cake. The amount of water carried is only slight and the most of water is discharged as a waste liquid. Since such waste liquid contains a large amount of high molecular organic materials such as carbohydrates and proteins in raw form, effective use of them will be advantageous from the standpoint of liquid-waste treatment.

The Martin's and Batter's methods are a method comprising the steps of kneading wheat flour with water to form dough or batter, aging it to thoroughly hydrate gluten, repeatedly washing the dough with added water, separating the gluten and starch milk (gluten wash liquid) and obtaining starch from the starch milk by such means as mechanical separation. In this case, the waste liquid contains the α-amylase inhibiting substance present in wheat flour. Thus such waste liquid can be a useful raw material for preparing the dieting agent of the invention.

α-Amylase inhibiting substances which are an active ingredient of the dieting agents of the invention are heat-resistant enzymatic substances and are not denatured when heated. This property is well utilized in the present invention for removal of protein contaminants and other enzymatic substances. When the supernatant in the above step (b) is heated at a temperature of 70 to 95° C., water- soluble proteins and other enzymatic substances undergo heat modification to mostly form muddy precipitates. Such modified proteins can be readily separated by means of standing or centrifugation. In this step, the content of the protein contaminants can be reduced to about $\frac{1}{3}-1/5$ without loss of α-amylase inhibiting substances.

Following step (b), the α-amylase inhibiting substance-containing solution is optionally subjected to the steps (c) and (d) for removing solid contaminants and microbial bodies if present.

One of the characteristic features in producing the dieting agent of the invention lies in the subsequent step (e). In this step, ultrafiltration is carried out to remove inorganic salts, saccharides, amino acids and other unnecessary low molecular weight substances while leaving a desired α-amylase inhibiting substances which are concentrated.

The ultrafiltration membranes used in the invention include those of polyacrylonitrile, polyolefin, polysulfone, polyimide or polypropylene materials, each having a fractionation molecular weight of 5,000, 6,000, 8,000, 10,000, 13,000, 20,000, 30,000, 50,000, 100,000 and 200,000 Dalton cut off. A polysulfone ultrafiltration membrane having a fractionation molecular weight of 20,000–100,000 Dalton cut off (e.g. PM-100 manufactured by Romicon Co., Ltd., NTU 35100 manufactured by Nitto Denko Co., Ltd.) is preferable in view of operativeness and concentration efficiency.

Subsequent to step (e), the concentrated solution is subjected to step (f), if necessary. This step (f) can produce a powdery material which is easily handled and stored.

Representative α-amylase inhibiting substances as prepared above have the following physical properties. Composition (per 100 g of the powders)

| Moisture | 2.3 g–3.3 g | (Vacuum heating-drying method) |
|---|---|---|
| Protein | 21.6 g–17.8 g | (Kjeldahl's method) |
| Ash | 5.6 g–7.8 g | (Direct incineration method) |
| Sodium | 624 mg–139 mg | (Atomic absorptiometry) |
| Potassium | 1.41 g–1.89 mg | (Atomic absorptiometry) |
| Magnesium | 356 mg–723 mg | (Atomic absorptiometry) |
| Chlorine | 1.43 g–737 mg | (Mohr's method) |
| Total saccharide | 57.5 g–56.1 g | (Somogyi's method) |
| Sulfate radical | 240 mg–620 mg | (Ion chromatography) |
| α-Amylase Inhibiting Activity | | (Blue starch method) |

-continued

| Saliva type | 5–1 U/mg solid |
|---|---|
| Pancreatic juice type | 3–0.1 U/mg solid |

The aqueous solution or solid substance containing the α-amylase inhibiting substances thus obtained can be used intact as a dieting agent, or may be further formulated into liquid preparations and solid preparations such as granules and tablets together with conventional adjuvants. The adjuvants include known excipients, fillers, lubricants, binders, perfumes, coloring agents and other additives.

For the purpose of using as a dieting agent, the preparations containing α-amylase inhibiting substances can be administered in the form of liquid, tablet or granule usually in an amount equivalent to 1,000 U or above, preferably 3,000–30,000 U of the saliva α-amylase inhibiting substance per day in adults.

The invention is further illustrated by the following non-limitative examples.

EXAMPLE 1

As the starting material was used a waste liquid of wheat flour from removal of gluten and starch. Inhibiting activity of the waste liquid was 8.41 for human saliva amylase (U/mg protein) and 3.55 for human pancreatic juice protein (U/mg protein). Into 800 lit. of the waste liquid were introduced steam over a period of 15 min. and the liquid was heated to 90° C. Subsequently, 900 lit. of the resulting solution were centrifuged continuously (3000 G) to remove modified proteins. The resulting clear supernatant was filtered with filters having a pore size of 3 μm and 1 μm, respectively to yield 850 lit. of a clear solution. The solution was then passed through a microfiltration membrane having a pore size of 0.2 μm for sterilization. The solution was then concentrated through Romicon PM-100 ultrafiltration membrane (membrane area of 2.5 m², two membranes) to about 1/10 of its original volume. A concentration temperature was 70° C., and an inlet pressure of the membrane was about 2 kg/m². The solution was circulated for about 3 hours.

Subsequently, the concentrated solution was spray-dried to yield 4.1 g of powders. Inhibiting activity of the product was 11.8 for human saliva amylase (U/mg protein) and 5.02 for human pancreatic juice amylase.

EXAMPLE 2

300 g of the powders obtained in Example 1 and 90 g of ethanol were kneaded in a conventional manner and the kneaded mass was granulated (0.8 mm) using an extrusion granulator, then dried and grated (20 mesh) to form granules.

EXAMPLE 3

300 g of the powders obtained in Example 1 and 75 g of 60% aqueous ethanol were kneaded by a conventional method. The kneaded mass was granulated (2 mm) using a crush granulator, dried and grated (1.2 mm). To the granules were added 9.0 g of sucrose fatty acid esters ("Ryoto Sugar Ester S-370" manufactured by Mitsubishi Kasei Corp.), and the mixture was tabletted by a conventional method to form tablets (about 300 mg/tablet).

EXAMPLE 4

Body weight gain-inhibiting effect in rats: (A) SPF Wistar rats (male) were bred with the commercially available rat feed MF (manufactured by Oriental Yeast Co., Ltd.). The feed had the composition of 8% moisture, 24.6% total protein, 5.6% total fat, 6.4% total ash, 3.1% fibrous substance, 52,3% soluble nitrogen-free material (carbohydrate) and 358 Kcal/100 g.

To two groups of each 5 rats were administered for 12 days 1 ml of distilled water alone for the control group and 1 ml of distilled water containing 2.5% of the powders obtained in Example 1 for the test group once a day through a stomach tube. Body weight was measured and the results are shown in the following table.

| Days elapsed | 0 | 6 | 12 |
| --- | --- | --- | --- |
| Control group | 205 g | 217 g | 238 g |
| Test group | 203 g | 212 g | 223 g |

(B) SPF Wistar rats (male) were bred with a standard feed (CLEA CE-2). The control group was given freely the standard feed, and the test group was given freely the standard feed additionally containing 5% of the powders obtained in Example 1. The test feed was given for 12 days.

The amount of the feed taken, amount of water taken and body weight were measured for the control group and the test group each consisting of 5 rats.

No significant difference in amount of the feed taken was observed between the control and test groups. There was also no great difference in amount of water taken.

Results of the body weight measurement are shown below.

| Days elapsed | 0 | 7 | 12 |
| --- | --- | --- | --- |
| Control group | 204 g | 218 g | 240 g |
| Test group | 206 g | 213 g | 226 g |

Acute Toxicity Test

To groups of each 5 ddY male and female mice (5 weeks age), were orally administered the aqueous extract of wheat flour (experimental section), raw wheat flour (control section) and distilled water (blank section) and the mice were observed for 14 days. The animals received the agent in 10% (w/v) aqueous solution at a dose of 50 ml/kg. No toxic symptoms was observed in any section. No significant difference in body weight change was measured for the three sections. Neither gross pathological change nor accumulation of the agent in viscera was also observed.

EXAMPLE 5

40% by weight of powders prepared in a similar manner as in Example 1 (inhibiting activity, 6.1 U/mg protein for human saliva α-amylase and 1.73 U/mg protein for human pancreatic juice α-amylase), 59% by weight of microcrystalline cellulose ("Abisel FD 101" manufactured by Asahi Kasei Corp.), 1% by weight of sucrose fatty acid esters ("Ryoto Sugar Ester S-370 F" manufactured by Mitsubishi Kasei Corp.) and a suitable amount of water were kneaded by a conventional method. The kneaded mass was granulated using a fluidized-bed drying granulator, and tabletted by a conventional method to form tablets, each weighing 250 mg. Each tablet had the inhibiting activity, 610 U for human saliva α-amylase and 172.5 U for human pancreatic juice α-amylase.

The tablets were administered to healthy humans 3 tablets 3 times a day immediately before meals. A total of 25 healthy humans were examined as the subject of a test. The administration was continued for two months and the variation in the body weight was observed. The results are shown in the following table.

All of the subjects (25 healthy humans) were subjected to hemanalysis before administration and 2 months after administration. No change was observed in all aspects of the items tested. Therefore the dieting agents of the invention will have no influence on the function of lever, pancreas and kidney.

| Subject (Female or Male) | Age | Height (cm) | Body weight before administration (kg) | Degree of obesity* before administration (%) | Reduced body weight (kg) | Degree of obesity 2 months after administration (%) |
| --- | --- | --- | --- | --- | --- | --- |
| A (F) | — | 156 | 73.0 | 31.0 | 3.0 | 28.0 |
| B (F) | — | 170 | 72.5 | 13.1 | 3.0 | 9.4 |
| C (F) | 29 | 156 | 51.7 | 2.5 | 2.0 | −1.4 |
| D (M) | 68 | 165 | 67.0 | 12.7 | 2.0 | 10.0 |
| E (M) | 30 | 168 | 74.0 | 17.3 | 2.0 | 15.0 |
| F (M) | 41 | 164 | 69.0 | 17.4 | 2.0 | 14.0 |
| G (M) | 33 | 168 | 78.0 | 21.5 | 5.0 | 16.2 |
| H (F) | 44 | 158 | 61.0 | 14.4 | 4.0 | 8.4 |
| I (F) | 52 | 153 | 52.0 | 8.3 | 3.0 | 2.7 |
| J (M) | 45 | 169 | 72.7 | 14.6 | 2.0 | 12.2 |
| K (M) | 70 | 165 | 68.0 | 14.0 | 3.0 | 10.0 |
| L (M) | 43 | 166 | 74.2 | 19.9 | 4.0 | 15.4 |
| M (F) | 56 | 164 | 97.0 | 40.6 | 5.0 | 37.4 |
| N (F) | 24 | 160 | 80.0 | 32.5 | 4.5 | 28.5 |
| O (F) | 46 | 165 | 63.0 | 7.1 | 7.0 | −4.5 |
| P (F) | 20 | 158 | 47.0 | −11.1 | 4.5 | −22.8 |
| Q (F) | 26 | 158 | 52.0 | −0.4 | 7.0 | −16.0 |
| R (F) | 33 | 165 | 75.5 | 22.5 | 4.5 | 17.6 |
| S (M) | 37 | 170 | 80.0 | 21.3 | 3.5 | 17.6 |
| T (M) | 27 | 163 | 74.0 | 23.4 | 6.5 | 16.0 |
| U (F) | 38 | 155 | 58.0 | 14.7 | 4.5 | 7.5 |
| V (M) | 31 | 174 | 76.0 | 12.4 | 4.5 | 6.9 |
| W (F) | 29 | 150 | 48.0 | 6.3 | 4.5 | −3.4 |
| X (F) | 50 | 157 | 62.0 | 17.3 | 6.0 | 8.4 |
| Y (F) | 21 | 160 | 56.0 | 3.6 | 5.0 | −5.9 |

| Subject (Female or Male) | Age | Height (cm) | Body weight before administration (kg) | Degree of obesity* before administration (%) | Reduced body weight (kg) | Degree of obesity 2 months after administration (%) |
|---|---|---|---|---|---|---|
| Average | | | | 15.1 | 4.1 | 9.1 |

*Degree of obesity (%) = $\frac{\text{Measured body weight} - \text{Ideal body weight}}{\text{Measured body weight}} \times 100$ Ideal body weight = (Height − 100) × 0.9

We claim:

1. A dieting agent comprising an aqueous solution or a solid substance of a concentrated α-amylase inhibiting substance which is produced by a process which comprises heat treating a supernatant fraction of an aqueous extract of wheat or wheat flour to modify unnecessary protein contaminants in the supernatant fraction, removing a modified protein from said fraction, subjecting a resulting aqueous solution containing an α-amylase inhibiting substance to a concentration treatment using an ultrafiltration membrane which allows passage of a fraction having a molecular weight of from 20,000 to 100,000 to form an aqueous solution of a concentrated α-amylase inhibiting substance or drying the aqueous solution.

2. A dieting agent of claim 1 wherein the aqueous solution containing an α-amylase inhibiting substance is subjected to a filtration and sterilization treatment prior to the concentration treatment using an ultrafiltration membrane.

3. A dieting agent of claim 1 wherein the α-amylase inhibiting substances are of the following composition per 100 g of the powders

| Moisture | 2.3 g–3.3 g | (Vacuum heating-drying method) |
|---|---|---|
| Protein | 21.6 g–17.8 g | (Kjeldahl's method) |
| Ash | 5.6 g–7.8 g | (Direct incineration method) |
| Sodium | 624 mg–139 mg | (Atomic absorptiometry) |
| Potassium | 1.41 mg–1.89 mg | (Atomic absorptiometry) |
| Magnesium | 356 mg–723 mg | (Atomic absorptiometry) |
| Chlorine | 1.43 g–737 mg | (Mohr's method) |
| Total saccharide | 57.5 g–56.1 g | (Somogyi's method) |
| Sulfate radical | 240 mg–620 mg | (Ion chromatography) |

4. A dieting agent of claim 1 wherein the α-amylase inhibiting substances are of the following α-amylase inhibiting activity (Blue starch method)

| Saliva type | 5–1 U/mg solid |
|---|---|
| Pancreatic juice type | 3–0.1 U/mg solid. |

5. A dieting agent of claim 1 wherein the aqueous solution of a concentrated α-amylase inhibiting substance is formulated into a liquid preparation together with conventional adjuvants.

6. A dieting agent of claim 1 wherein the solid substance of a concentrated α-amylase inhibiting substance is formulated into a solid preparation such as granule and tablet together with conventional adjuvants.

7. A dieting agent of claim 1 wherein the preparations containing alpha-amylase inhibiting substances are administered in the form of liquid, tablet or granule usually in the amount equivalent to 1,000 U–30,000 U [of 200 mg to 30 g]of the saliva alpha-amylase inhibiting substance per day in adults.

8. A dieting agent of claim 7 wherein the amount of alpha-amylase inhibiting substance is equivalent to 3,000–30,000 U per day in adults.

9. A dieting agent comprising an aqueous solution or a solid material of a concentrated alpha-amylase inhibiting substance comprising a fraction having a molecular weight of 20,000 to 100,000.

10. A dieting agent comprising, as active ingredient, an amount equivalent to 1,000–30,000 U of an alpha-amylase inhibiting substance having a molecular weight of from 20,000 to 100,000.

11. A dieting agent according to claim 10 wherein the amount of active ingredient is in the range of 3,000–30,000 U.

12. The use of an alpha-amylase inhibiting substance of a molecular weight of 20,000 to 100,000 as an active ingredient in a dieting agent.

* * * * *

UNITED STATES PATENT AND TRADEMARK OFFICE
CERTIFICATE OF CORRECTION

PATENT NO. : 5,093,315
DATED : March 3, 1992
INVENTOR(S) : MAEDA ET AL

It is certified that error appears in the above-indentified patent and that said Letters Patent is hereby corrected as shown below:

On the title page: Item [73] Amend the Assignee to read --
Nisshin Flour Milling Co., Ltd. and Yakurigaka Chuo Kenkyusho
Co., Ltd. --.

Signed and Sealed this

First Day of March, 1994

*Attest:*

BRUCE LEHMAN

*Attesting Officer*     *Commissioner of Patents and Trademarks*